United States Patent

Mitro et al.

[11] Patent Number: 5,922,179
[45] Date of Patent: Jul. 13, 1999

[54] APPARATUS FOR ETCHING AND COATING SAMPLE SPECIMENS FOR MICROSCOPIC ANALYSIS

[75] Inventors: Richard J. Mitro, San Ramon; Reza Alani, Pleasanton; Leszek Malaszewski, Walnut Creek, all of Calif.

[73] Assignee: Gatan, Inc., Pleasanton, Calif.

[21] Appl. No.: 08/954,080

[22] Filed: Oct. 20, 1997

Related U.S. Application Data

[60] Provisional application No. 60/033,495, Dec. 20, 1996.

[51] Int. Cl.$^6$ .................................................. C23C 14/34
[52] U.S. Cl. ............................... 204/298.04; 204/192.11; 204/298.36; 204/192.34
[58] Field of Search ........................ 204/298.04, 192.11, 204/298.36, 192.34, 298.12, 192.12, 192.15, 192.26, 298.28

[56] References Cited

U.S. PATENT DOCUMENTS

| | | |
|---|---|---|
| 4,272,682 | 6/1981 | Swann . |
| 4,340,815 | 7/1982 | Franks . |
| 4,510,386 | 4/1985 | Franks . |
| 4,793,908 | 12/1988 | Scott et al. ..................... 204/192.26 |
| 4,913,789 | 4/1990 | Aung . |
| 4,923,585 | 5/1990 | Krauss et al. ..................... 204/298.04 |
| 4,992,398 | 2/1991 | Deutchman et al. ............. 204/298.04 |
| 5,009,743 | 4/1991 | Swann . |
| 5,091,049 | 2/1992 | Campbell et al. . |
| 5,178,957 | 1/1993 | Kolpe et al. . |
| 5,292,419 | 3/1994 | Moses et al. ..................... 204/298.28 |
| 5,336,550 | 8/1994 | Ganapathi et al. . |
| 5,472,566 | 12/1995 | Swann et al. . |
| 5,488,528 | 1/1996 | Chen et al. . |
| 5,628,659 | 5/1997 | Xie et al. ......................... 204/298.04 |
| 5,633,502 | 5/1997 | Fischione . |
| 5,650,378 | 7/1997 | Iijima et al. ..................... 204/192.11 |

FOREIGN PATENT DOCUMENTS

| | | |
|---|---|---|
| 224 878 A1 | 7/1985 | Germany . |
| 625 641 A5 | 9/1981 | Switzerland . |

OTHER PUBLICATIONS

Ion Tech Ltd. brochure, B365 EM Microworkshop, 1982.
Gatan brochure, Model 600 DuoMill.
Gatan brochure, Model 681 High Resolution Ion Beam Coater.
Gatan brochure, Model 691 Precision Ion Polisher.
Gatan KnowHow brochure, May 1997.

*Primary Examiner*—Nam Nguyen
*Assistant Examiner*—Gregg Cantelmo
*Attorney, Agent, or Firm*—Killworth, Gottman, Hagan & Schaeff, LLP

[57] ABSTRACT

An apparatus and process for the etching and coating of samples in a single vacuum chamber, thus minimizing handling and transfer of the samples is provided. The apparatus includes a sealed chamber and a vacuum pump for forming and maintaining a vacuum in the chamber, a first ion gun positioned in the chamber to etch a sample, a sputtering target in the chamber, and at least one additional ion gun positioned in the chamber to cause material from the target to be directed onto the sample.

14 Claims, 5 Drawing Sheets

APPARATUS FOR ETCHING AND COATING SAMPLE SPECIMENS FOR MICROSCOPIC ANALYSIS

CROSS REFERENCE TO RELATED APPLICATIONS

This patent application claims the benefit of U.S. Provisional Application Serial No. 60/033,495, filed Dec. 20, 1996.

BACKGROUND OF THE INVENTION

The present invention relates to an apparatus for both etching and coating a specimen prior to analysis, and more particularly to an ion beam etching and sputter coating system for the preparation of sample specimens to be analyzed in a microscope.

Ion milling systems are used extensively for etching, milling, cutting, and cleaning samples of various materials such as ceramics, semiconductors, metals, and combinations thereof to make possible and/or enhance certain features for analysis in a microscope, typically analysis with an electron or optical microscope. Many of these samples, particularly samples of electrically insulating materials, are coated after cleaning or etching and prior to examination in an electron or optical microscope to prevent charging effects. Certain coatings also have the effect of increasing the secondary electron yield from almost all types of material.

Typically for etching and coating, the samples to be studied are first mounted to a sample holder for the purpose of mechanically polishing one or more surfaces until such surfaces are flat, parallel, and scratch free. The polished sample is then removed from the polishing holder, mounted to a second holder, and placed into an ion milling device for etching. In the ion mill, the sample is positioned in the path of one or more ion beams and etched at a relatively steep angle between the incident beam(s) and the sample surface.

Once etching has been completed, the sample may require remounting to a third holder to enable installation into a separate device for the purpose of depositing a conductive coating thereon. Previously, such coatings were applied by such techniques as thermal evaporation, arc discharge, and diode, magnetron, or RF sputtering. More recently, the coatings have been applied by sputter coating in a vacuum using ion beam techniques.

After coating, the sample may be mounted to a final stub or holder designed for use in a specific microscope, for example a transmission electron microscope, a scanning electron microscope, or even a light microscope. Thus, the current techniques for sample preparation require that the samples be handled multiple times and transferred among several instruments and vacuum systems. These techniques expose the samples to potential damage and/or contamination of the sample surface.

Accordingly, there is a need in the art for a process and system which minimizes sample handling and exposure to potential damage and/or contamination.

SUMMARY OF THE INVENTION

The present invention meets that need by providing for the etching and coating of samples in a single vacuum chamber, thus minimizing handling and transfer of the samples. In accordance with one aspect of the invention, an apparatus for the precision etching and coating of a sample is provided and includes a sealed chamber and a vacuum system for forming and maintaining a vacuum in the chamber. The apparatus also includes a sample holder and an airlock for moving samples quickly into and out of the chamber.

An ion milling gun is positioned in the chamber to direct a stream of ions, neutrals, or combinations thereof onto the sample to etch the sample. Also in the chamber, at least one movable sputtering target is positioned for coating purposes. The target is shielded from the ion and neutrals stream emanating from the milling gun during etching. To coat the sample, at least one additional ion gun is positioned to direct a stream of ions and neutrals onto the target. After etching of the sample, the target is moved into a position in the chamber where material sputtered from it becomes coated onto the sample.

In a preferred embodiment, there are two ion guns positioned to direct streams of ions and neutrals from different angles to impact the target and sputter deposit material from the target onto the sample. The moveable target may be positioned to aid in efficiently directing sputtered material onto the sample.

In accordance with another aspect of the invention, a process is provided for the etching and sputter coating a sample in a single evacuated chamber without the need to remove the sample or break the vacuum during processing. The process includes the steps of mounting the sample onto a sample holder and then loading the sample and holder into the evacuated chamber. The sample is etched using an ion milling gun. Then, the sample may be immediately coated in the same chamber without any need for further handling or transfer using a target material and additional sputtering ion gun or guns which are provided in the chamber.

After moving the target into position, the ion gun or guns are energized and produce energetic ions and neutrals which impinge onto the target and cause target material to be sputter deposited onto the sample. The coated sample may then be removed from the chamber. With the airlock, there is no need to continually cycle the pressure in the chamber from atmospheric to vacuum and back. Rather, the vacuum need be formed only once and then maintained.

By performing the etching and coating operations in the same chamber, the sample is not moved or handled between process steps, which minimizes the amount of contaminants to which the sample may be exposed. Further, the sample may be initially mounted onto a sample holder and then supported by that same holder throughout the entire etching/coating process. The same holder may even be used to support the sample for microscopic analysis.

In a preferred embodiment of the process, the sample is initially mounted onto a holder and then mechanically polished. The polished sample is then transferred into the vacuum chamber through an airlock where it is etched and then coated. The finished, coated sample is then removed from the vacuum chamber ready for viewing in a selected microscope.

The system and process of the present invention has some utility in sample preparation for scanning electron microscope (SEM) analysis, transmission electron microscope (TEM) analysis, and light microscope observations analysis. Accordingly, it is a feature of the present invention to provide for the etching and coating of samples in a single device under vacuum, thus minimizing handling and transfer of the samples. This and other features and advantages of the invention will become apparent from the following detailed description, the accompanying drawings, and the appended claims.

DETAILED DESCRIPTION OF THE PREFERRED EMBODIMENT

Figure 1:
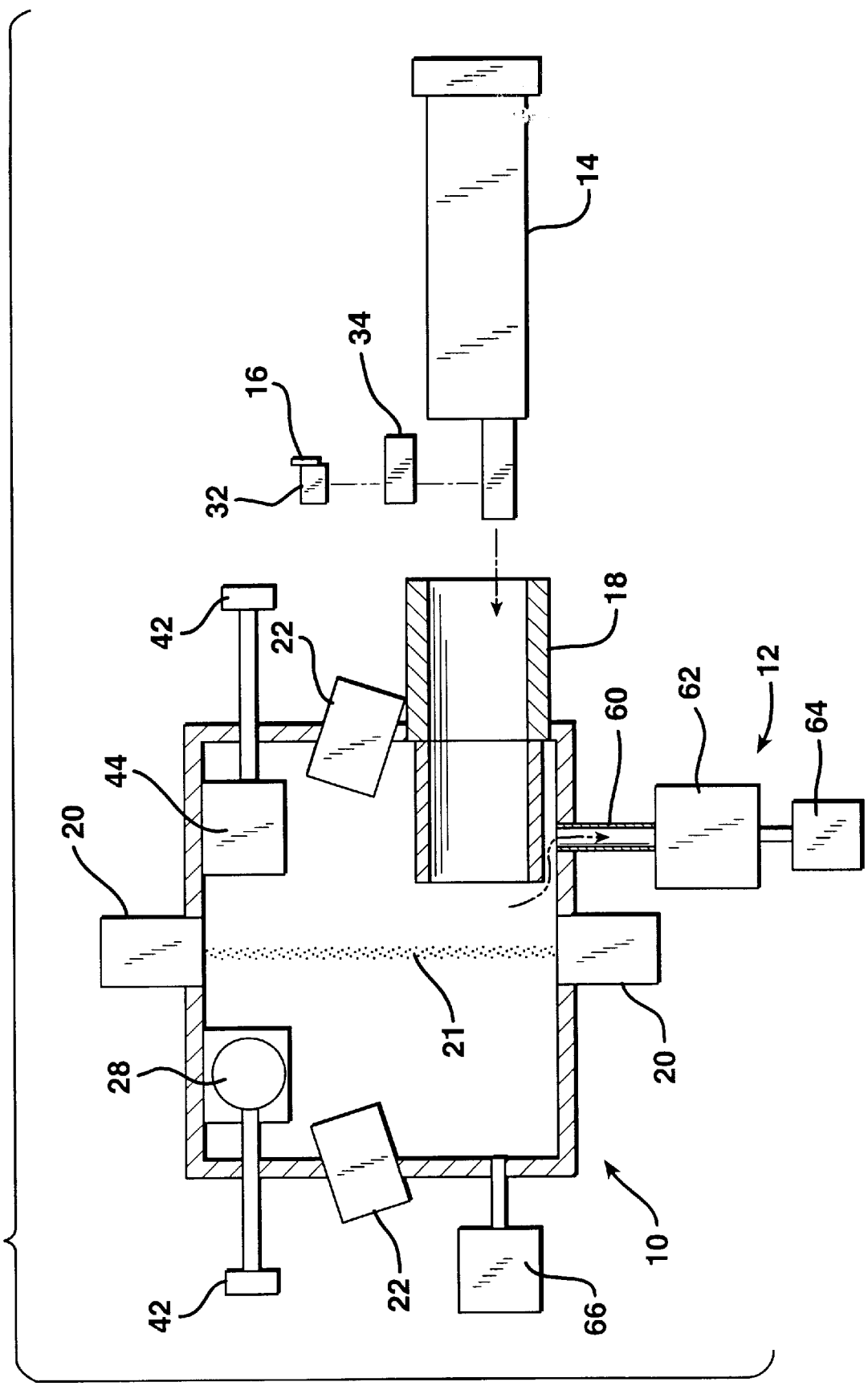
FIG. 1 is a schematic side view of the system of the present invention with the sample and sample holder positioned outside the chamber.

With reference to FIG. 1, the etching and coating system of the present invention includes a sealed chamber 10 which is evacuated by vacuum system 12 to provide a working vacuum pressure in the chamber. A sample holder 14 is used to mount a sample 16 thereon. Sample holder 14 may be cooled, such as by for example using liquid nitrogen, to reduce or maintain the temperature of sample 16 within a predetermined range as taught by Jones et al, U.S. Pat. No. 4,950,901, the disclosure of which is hereby incorporated by reference.

Depending upon the sample and the desired type of microscopic analysis instrument, it may be desirable to polish the sample mechanically prior to insertion into vacuum chamber 10. Commercial mechanical polishing devices are readily available and are used to grind and polish one or more of the sample surfaces until they are flat, parallel, scratch free, and of a desired thickness.

The polished sample 16, mounted on holder 14, is then inserted into vacuum chamber 10 through airlock 18 to position the sample beneath ion etch gun 20. Airlock 18, in a preferred embodiment, is pneumatically controlled to provide fast loading and unloading (i.e., 30 seconds) of the sample. By using an airlock, the vacuum chamber 10 is only vented for routine servicing, allowing the base vacuum pressure to be maintained. A pneumatically-controlled airlock is described in Swann, U.S. Pat. No. 4,272,682.

Airlock 18 may vary in size and shape and may be designed to accept various configured sample holders as in the case of etching or coating TEM samples while mounted in a TEM holder or when a probe is used for monitoring the rate of sputtered coating deposition and total coating thickness. TEM sample holders vary in size and configuration according to manufacturer. Thus, rather than manufacture separate airlocks 18 to fit each sample holder, a removable assembly may be provided into which sample holders of various preselected sizes and configurations may be inserted. Such a removable assembly comprises a reducing sleeve 52 and interchangeable adaptors 54 (only one shown), as illustrated in FIG. 5, which enable the accommodation of TEM sample holders of all varieties.

Figure 4:
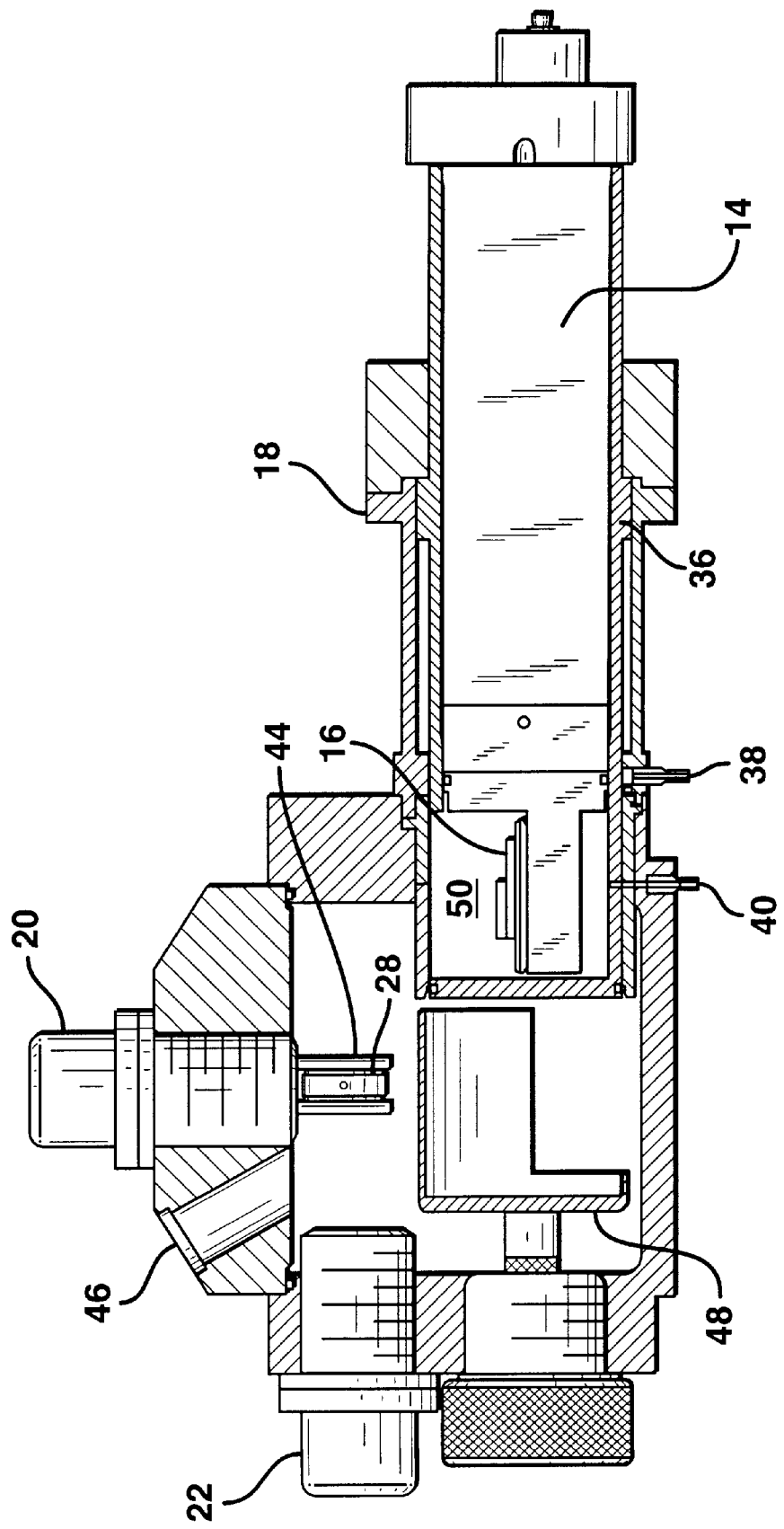
FIG. 4 is a side view, in partial section, illustrating the target and sample holder in retracted positions.
Figure 5:
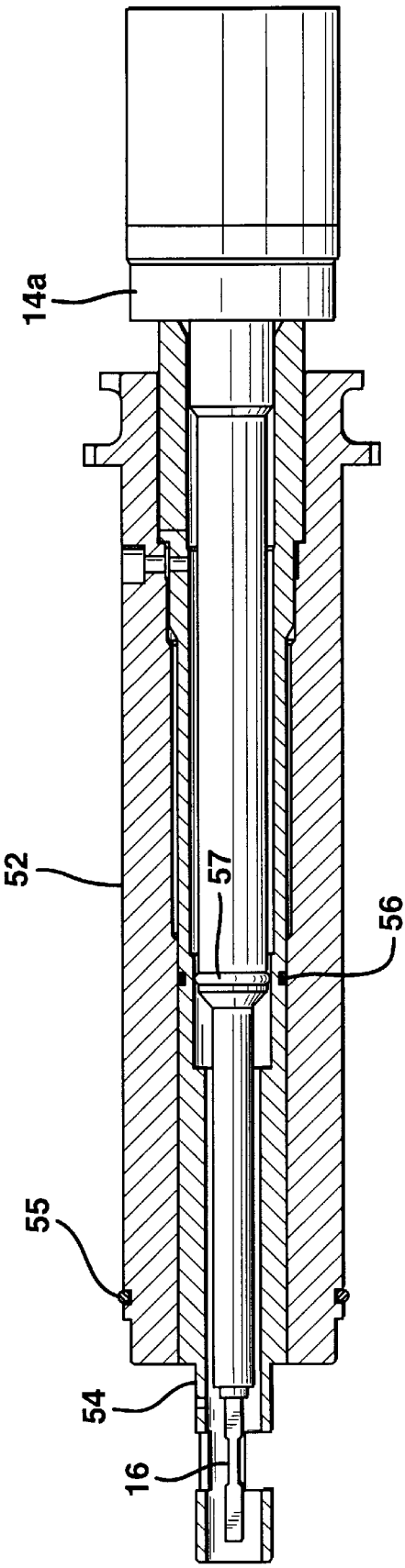
FIG. 5 is a side view, in partial section, illustrating features of a TEM sample holder.

Referring to FIG. 5, reducing sleeve 52 has a generally cylindrical configuration and the same outer dimensions as a conventional sample holder 14 (see FIG. 1) which it replaces. Sleeve 52 also has an inner diameter sized and adapted to fit the fixed outer diameter of an interchangeable adaptor 54. Interchangeable adaptors 54 have an inner diameter sized and adapted to accept TEM sample holders of various sizes and configurations such as sample holder 14a illustrated in FIG. 5. Thus, the reducing sleeve and adaptor assembly fits into airlock 18 as shown in FIG. 5. O-ring 55 provides a vacuum tight seal between adaptor 54 and the inner wall of pneumatic airlock piston 36 (shown in FIGS. 3 and 4).

O-ring 57 provides a vacuum tight seal between adaptor 54 and sleeve 52. Sample holder 14a is fitted into adaptor 54 with a vacuum tight seal being provided by O-ring 57 in sample holder 14a. When in position, the portion of the TEM sample holder 14a which contains the sample 16 itself is extended into sealed chamber 10 (see FIG. 1) by the operation of airlock 18. While in chamber 10 (see FIG. 1), sample 16 is exposed to the ion beam for etching or to the sputtered target material 30 for coating. Thus, a user can process TEM samples using sample holders of various manufacturers simply by interchanging adaptors 54.

Figure 3:
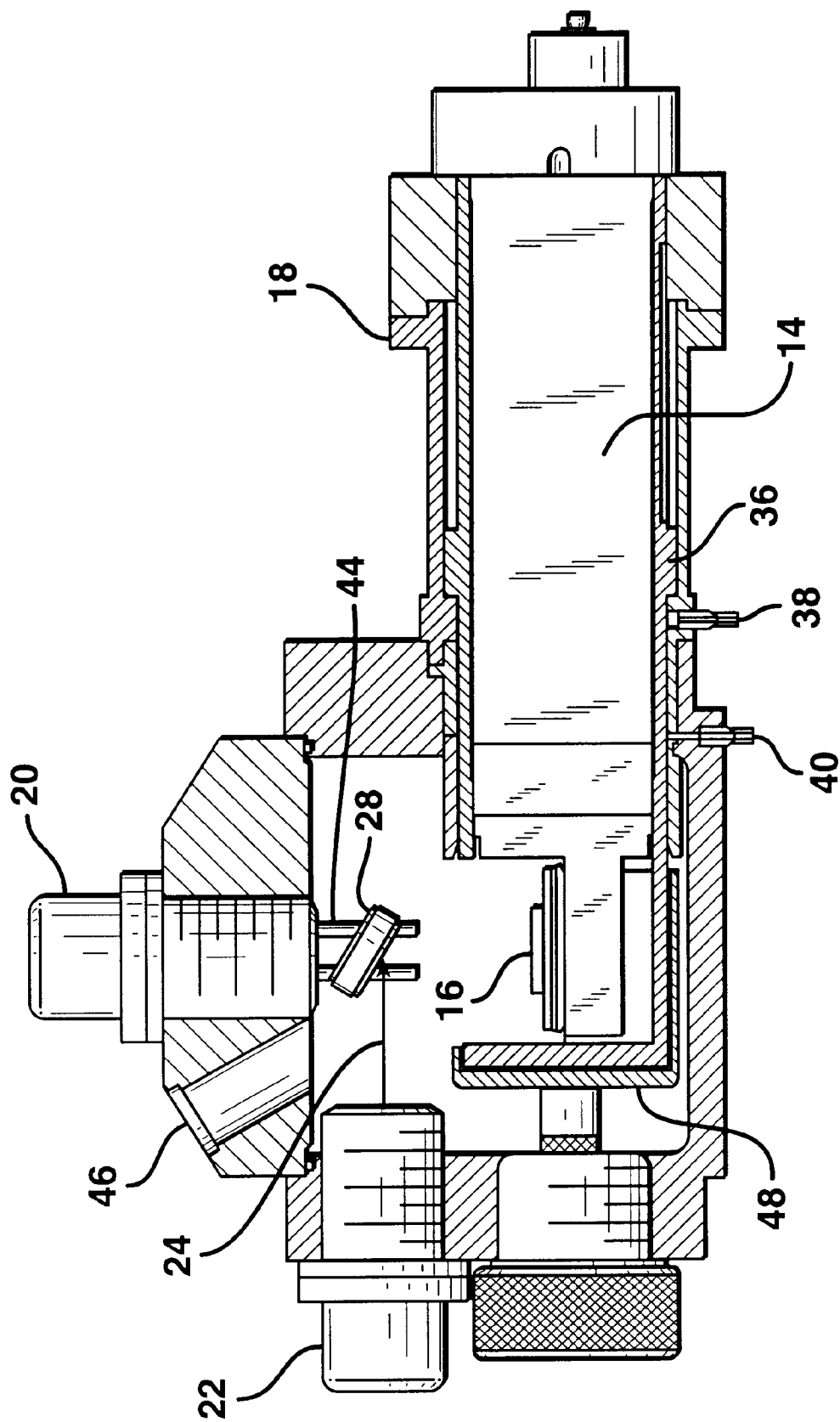
FIG. 3 is a side view, in partial section, illustrating the target and sample holder in position for sputter coating.

As shown in FIG. 1, sample 16 is secured to a sample mount 32, and mount 32 is inserted into a sample adaptor 34. The entire assembly is then inserted into sample holder 14. As best shown in FIGS. 3 and 4, sample holder 14 is housed in airlock 18 and is moved into and out of position by a pneumatic piston 36. Gas pressure is provided to the piston from a source of compressed gas (not shown) connected through port 38. Airlock vacuum is achieved by connection 40 which communicates with a vacuum pump (not shown).

Sample holder 14 may be designed to either "rock or rotate" or "rock and rotate" during the etching, cleaning, and/or coating processes. Such rocking and/or rotating mechanisms are known in this art. Rotation of the sample during etching produces a more uniformly etched sample surface and a more uniform etching rate. Rocking and rotating the sample during coating produces homogeneous coatings of uniform thickness. A fixed rock angle may be selected to change the incident angle of the ion beam on the sample surface from an angle normal to the sample surface to that of a lesser angle. The fixed angle also helps to increase the size of the etched area when combined with rotation.

Also in FIG. 1, an ion etch gun 20 is positioned in chamber 10 as shown to provide the relative beam angle between the incident beam 21 and the sample surface. Gun 20 may be mounted at the top of chamber 10 as shown, or at the bottom, or at a location which would provide angled etching of the sample. Further, gun 20 may be positioned so as to vary the distance between the gun and the surface of the sample. That is, gun 20 may be moved inwardly or outwardly from its position on the chamber wall. Moving gun 20 closer to the sample surface has the effect of increasing the etch rate for a given gun energy (keV). Such increased etch rate is useful where the gun is used for slope cutting of a sample or TEM sample milling.

Additionally, gun 20 may be mounted such that it is able to pivot. This provides the ability to change the angle at which the energetic ions and neutrals impinge the sample surface for a fixed, horizontally oriented sample. Thus, the angle of ion impingement could be adjusted without moving the sample.

A number of ion etching or ion milling guns are readily commercially available. For example, ion gun 20 may comprise a grounded cathode and an anode connected to an adjustable high voltage supply (not shown). A gas or combination of gases, typically any noble or inert gas such as argon or xenon, may be supplied to the gun from a separate source 66. The high voltage discharge between the anode and cathode generates and directs an energetic beam 21 of ions and neutrals towards sample 16 (when sample 16 is in the position shown in FIG. 2). Ion etch gun 20 may also comprise a rare earth magnet Penning gun which is capable of delivering a high current density ion beam which produces a high sample etching rate, reducing etching time.

Optionally, a second ion gun 20 may be positioned on the opposite side of chamber 10 as shown. Such a second gun would be able to provide simultaneous two-sided milling of samples for transmission electron microscopy (TEM). The ion gun or guns 20 may also be used to provide re-milling or cleanup of TEM samples which were initially prepared by broad ion beam (BIB) milling or focused ion beam (FIB) milling, or mechanically thinned using a known wedge technique. Such samples, still mounted in a TEM holder, may be thinned using one or more ion guns to mill at shallow angles.

The ion gun or guns 20 may also be used not only to clean (etch) stand-alone TEM samples but also samples mounted in a TEM sample holder, thus cleaning both the sample and holder simultaneously or cleaning the holder only. Such a cleaning improves high resolution imaging by removing amorphous layers and carbon-containing contaminants from the sample (and holder) surface by exposure to the etching beam at selected keV energies.

Figure 2:
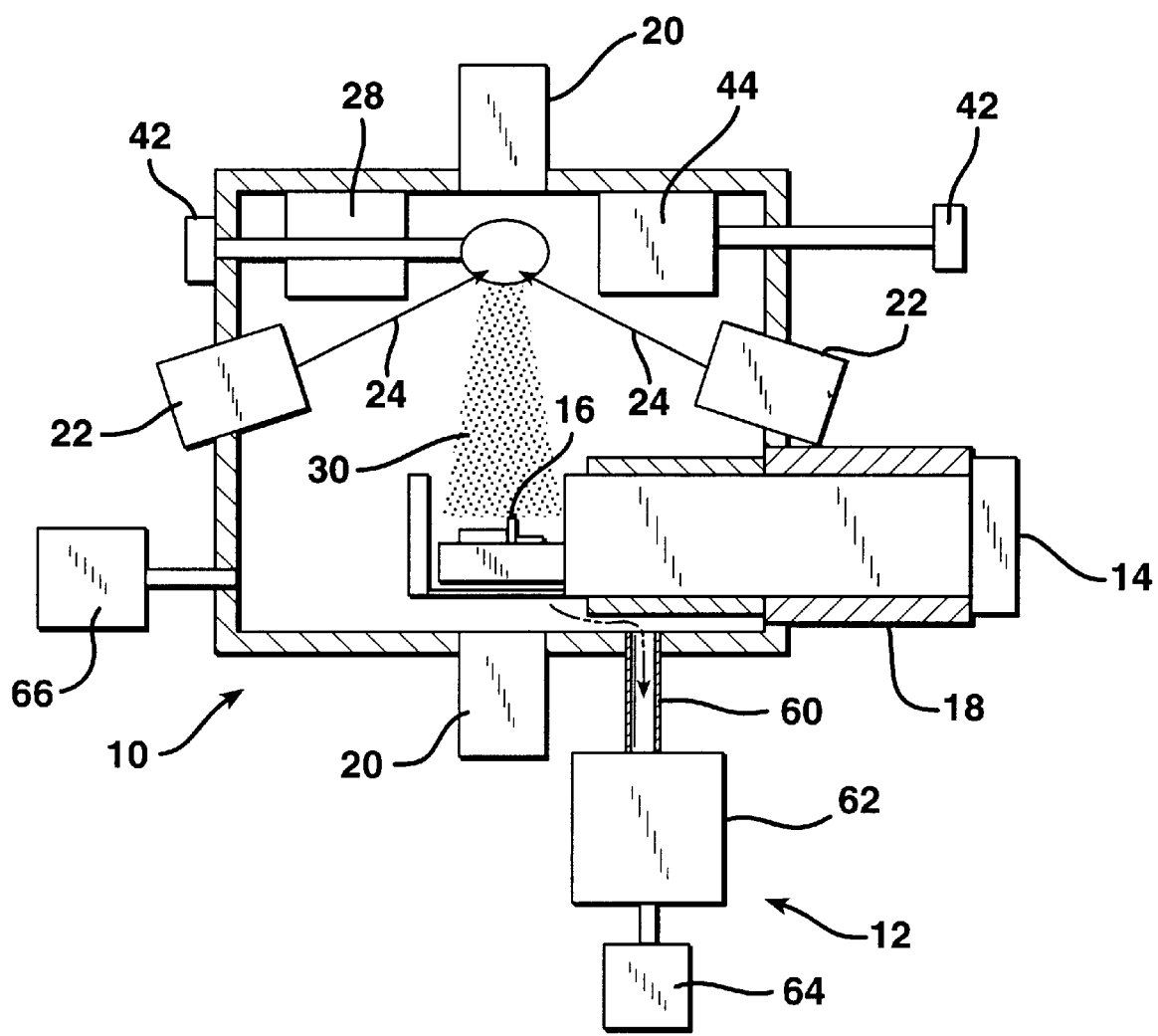
FIG. 2 is a schematic side view of the system with the sample and holder therein, and the system operating in a sputter deposit mode to coat the sample.

During etching of the sample, target or targets 28 are maintained in a shielded location (FIGS. 1 and 4) out of the path of the ion beam. As best illustrated in FIGS. 1–2, targets 28 are carried on the tip of a retractable piston assembly 42 and can be moved from a retracted position (FIG. 1) out of the path of the ion gun to an extended position (FIG. 2). When in a retracted position, targets 28 are shielded on both sides by target shields 44. (also shown in FIGS. 3 and 4)

As can be seen in FIGS. 1 and 2, located on chamber 10 is a vacuum system 12 which includes a drag pump manifold 60 which is in turn connected to molecular drag pump 62. Molecular drag pump 62 provides a suitable vacuum level for the operation of the ion guns by providing an ultimate vacuum of $10^{-6}$ torr in sealed chamber 10. Molecular drag pump 62 will not operate properly unless its outlet is prepumped; therefore it is necessary to reduce its foreline or outlet vacuum. This is accomplished by backing molecular drag pump 62 with an oil free diaphragm pump 64. The oil free system is preferred to eliminate the possibility of introducing hydrocarbon contamination from the lubricating oils of the pump into sealed chamber 10.

As also shown in FIGS. 3 and 4, chamber 10 may include a viewing window 46. Window 46 provides an operator with a quick visual inspection of the working portion of vacuum chamber 10 to verify the correct operation of the device during rocking and/or rotation of the sample, the correct operation of the ion guns during etching or coating, and the correct positioning of shutter 48. Importantly, the window also permits viewing of the sample to insure that it is properly positioned, has not slipped from its holder or mount, has not changed angle during movement of the holder or during loading or unloading through the airlock.

With reference again now to FIG. 2, once etching of the sample is completed, ion etch gun 20 is turned off, and one of the targets 28 is moved into position. One or more ion sputter guns, such as, for example, the pair of ion sputter guns 22 are activated and direct energetic beams of ions and neutrals at the target. Ion sputter guns may operate in the same general manner as ion etch gun 20. In a preferred embodiment of the invention, ion sputter guns 22 comprise rare earth magnet, Penning ion guns.

Penning ion guns provide a high density ion flux and operate over a broad range of ion energies. Penning ion guns are advantageous as well in that they have low maintenance requirements, with no need for replacement of parts. The sputter deposits produced from the ion guns is high quality and amorphous.

In a typical arrangement, a sample, such as a ceramic or semiconductor material, will be coated with a thin, amorphous layer of a conductive material. For example, target 28 may comprise chromium, platinum, gold-palladium, iridium, tungsten, carbon, etc. Ion beams 24 from ion guns 22 cause target material 30 to be sputter deposited onto sample 16. The thickness of the deposited coating may be monitored using conventional techniques. Generally, the target may be sputter cleaned prior to deposition of the coating for a short initial period by exposing it to the energized stream of ions and neutrals.

As shown in greater detail in FIGS. 3 and 4, there may be an independent rotatable shutter 48 so that the sample is protected during cleaning of the target. FIG. 3 illustrates the target in an extended working position such that the energized beam 24 contacts target 28 to sputter deposit material onto sample 16. In FIG. 3, rotatable shutter 48 is in an "open" position to expose the sample for coating.

Referring now to FIG. 4, target 28 is shown in a retracted, shielded position as it would be during the etching procedure, and shutter 48 has been rotated to a "closed" position which can also be used to isolate the sample. Shutter 48 preferably comprises an electrically conductive material such as a metal which permits it to act as a Faraday cup or cage. By suitable connections (not shown), shutter 48 may also be used to monitor the ion current from first ion gun 20. Also, for purposes of understanding and illustration, the sample holder is shown in a retracted position within airlock chamber 50, and shutter 48 has been rotated to a "closed" position.

Referring to FIG. 1, once a desired coating thickness is attained, the ion guns are turned off, and the sample is removed from chamber 10 through airlock 18. As the sample is already mounted on a suitable stub or mount 32, the sample may be loaded into or taken directly to a desired microscope for analysis. The apparatus and process of the present invention provide a technique which reduces sample handling and transfer to a minimum number of steps and substantially reduces the possibility of sample damage.

The precision etching and coating system of the present invention may be used for ion beam slope cutting of samples. This is accomplished by using ion gun 20 and fixing the angle of a screened-mount sample holder to cross cut sections through heterogeneous solids such as, for example, integrated circuits and various semiconductor electronic devices. The screen which is mounted onto the sample holder comprises, for example, a block of metal having one or more sharply-defined knife edges. The metal of the screen serves as a protective mask for portions of the sample, while exposed areas of the sample are etched away. This provides the ability to investigate the cross-sectional microstructure of a device to reveal regions deep inside of the material for SEM observations and microanalysis. Once sufficiently etched, the sample is immediately sputter coated in chamber 10 with a desired target material using ion guns 22.

The system of the present invention may also be used to wire shadow a TEM sample by cross sectioning the sample without glue line preparation. Again, once sufficiently etched, the sample is immediately sputter coated in chamber 10. While both beam slope cutting and wire shadowing are known techniques, the present system permits the etched and cut samples to be immediately sputter coated in the same vacuum chamber without needing to move the samples.

The precision etching and coating system may also be used with chemical etching processes using non-inert gases such as reactive ion beam etching (RIBE) and chemically-assisted ion beam etching (CAIBE). In this embodiment, such non-inert gases, and combinations thereof, may be supplied to chamber 10 through an external source such as source 66 (as shown in FIGS. 1 and 2). Halogens and halogen-containing gases as well as oxidants such as oxygen and oxygen-containing gases and combinations of such gases including $I_2$, $Cl_2$, $Br_2$, $N_2O_4$, $CF_4/O_2$, etc. produce superior results for special materials used in the semiconductor industry. After etching, either by RIBE or CAIBE, the sample may be immediately sputter coated using the target material and ion guns 22.

The system of the present invention may also be used to sputter coat metallographic samples for micro-hardness tests and light microscope applications.

While certain representative embodiments and details have been shown for purposes of illustrating the invention, it will be apparent to those skilled in the art that various changes in the methods and apparatus disclosed herein may be made without departing from the scope of the invention, as defined by the accompanying claims.

We claim:

1. An apparatus for the precision etching and coating of a sample for microscopic analysis comprising: a chamber communicating with a source of vacuum to form and maintain a vacuum in said chamber; a sample holder; an airlock in said chamber through which said sample holder is loaded and removed; a first ion gun positioned in said chamber to etch a sample mounted on said sample holder; a sputtering target in said chamber and a shield in said chamber for shielding said sputtering target; and at least one additional ion gun positioned in said chamber to cause material from said target to be directed onto said sample, said sputtering target being movable from a first shielded position out of a path of a stream of ions and neutrals emanating from said at least one additional ion gun to a second position in the path of said stream.

2. An apparatus as claimed in claim 1 in which said sample holder is cooled to reduce or maintain a temperature of said sample within a predetermined range.

3. An apparatus as claimed in claim 1 including a viewing window in said chamber.

4. An apparatus as claimed in claim 1 in which said first ion gun is adjustable to vary a distance between said ion gun and a surface of said sample.

5. An apparatus as claimed in claim 1 in which said first ion gun is pivoted to alter an angle of impact of a stream of ions and neutrals onto a surface of said sample.

6. An apparatus as claimed in claim 1 in which each of said sputtering targets is mounted to a retractable piston assembly.

7. An apparatus as claimed in claim 1 including a shutter in said chamber movable from a first position shielding said sample to a second position out of a path of a stream of ions and neutrals emanating from said first ion gun.

8. An apparatus as claimed in claim 7 in which said shutter comprises an electrically conductive material which acts as a Faraday cup.

9. An apparatus as claimed in claim 8 in which an ion current from said first ion gun is monitored by said shutter.

10. An apparatus as claimed in claim 1 in which said source of vacuum comprises an oil-free vacuum system including a molecular drag pump in combination with a diaphragm pump.

11. An apparatus as claimed in claim 1 further comprising a removable assembly which, in conjunction with said airlock, permits insertion and removal of sample holders of preselected sizes and configurations.

12. An apparatus as claimed in claim 11 in which said removable assembly comprises a generally cylindrical reducing sleeve and a generally cylindrical interchangeable adaptor, said reducing sleeve having an inner diameter sized and adapted to fit the outer diameter of said generally cylindrical interchangeable adaptor.

13. An apparatus as claimed in claim 12 in which said generally cylindrical interchangeable adaptor has an inner diameter which is sized and adapted to fit said sample holders.

14. An apparatus as claimed in claim 1 in which said sample holder includes a screened mount thereon, said screened mount comprising a block having one or more sharply-defined edges.

* * * * *